United States Patent [19]
Kochinsky

[11] Patent Number: 4,994,280
[45] Date of Patent: Feb. 19, 1991

[54] IODOPHOR COMPOSITION FOR AQUACULTURE

[76] Inventor: Lyle J. Kochinsky, 310 SE. 3rd Terr., Dania, Fla. 33004

[21] Appl. No.: 372,659

[22] Filed: Jun. 20, 1989

[51] Int. Cl.$^5$ .............................................. A61K 33/36
[52] U.S. Cl. ..................................... 424/672; 424/667
[58] Field of Search .................................. 424/667, 672

[56] References Cited

U.S. PATENT DOCUMENTS

| | | | |
|---|---|---|---|
| 2,977,315 | 3/1961 | Schelb | 252/106 |
| 3,028,299 | 4/1962 | Winicov | 167/17 |
| 3,220,951 | 11/1965 | Canter | 252/106 |
| 3,274,116 | 9/1966 | Mills | 252/106 |
| 3,277,010 | 10/1966 | Schenck | 252/106 |
| 4,148,884 | 4/1979 | Thorogood | 424/150 |
| 4,207,310 | 6/1980 | Langford | 424/150 |
| 4,597,975 | 7/1986 | Woodward et al. | 424/672 |
| 4,759,931 | 7/1988 | Van Paassen | 424/150 |

OTHER PUBLICATIONS

Chem. Abst. 74: 45370t (1971), Taylor et al.

Primary Examiner—Stanley J. Friedman
Assistant Examiner—Zohreh A. Fay
Attorney, Agent, or Firm—Alvin S. Blum

[57] ABSTRACT

A stable concentrated iodophor composition is useful in aqueous solution for control of microorganisms in the therapeutic and prophylactic culture of aquatic animals such as fish, reptiles, and amphibians. It is effective against bacteria, fungi, viruses, algae and the like in very dilute solution while being non-toxic to higher animals. Its biocidal action is due in large measure to the action of iodine that is slowly released into the water. The solution has low-foaming properties to enable its use with water systems having moving water in fountains, filters and bubble aerators. The composition includes phosphoric acid, ethylene glycol monobutyl ether, and two iodophors, a first iodophor formed by mixing iodomethane with a quaternary ammonium surfactant and a second iodophor formed by heating iodine with either an alkyl phenoxyl polyether alcohol or oleic acid sulfonate.

5 Claims, No Drawings

IODOPHOR COMPOSITION FOR AQUACULTURE

FIELD OF THE INVENTION

This invention relates to iodophors useful in combatting microorganisms and more particularly to novel iodine compositions useful in combatting harmful microorganisms in the culture of higher animals that live in an aqueous environment.

BACKGROUND OF THE INVENTION

Animals that live in a water environment such as fish, turtles, frogs and the like are subject to infections from various microorganisms such as fungi, virus, bacteria, algae and the like. Furthermore the water container may become unsightly from overgrowth of certain of these organisms.

Whereas topical treatment of terrestrial animals is relatively simple, this is ineffective with animals in an aquatic environment. Iodophors which slowly release iodine have been recognized as useful germicidal and disinfecting agents with effectiveness against a broad range of microorganisms through the biocidal action of iodine. Iodophors have been the subject of many U.S. patents. None of these are directed to the special problems presented by the aquatic environment in which certain higher animals must live. The iodophor composition must be stable in concentrated form yet effective against microorganisms when greatly diluted by water. It must be resistant to foaming, especially where the water is in motion such as in filters and bubble aerators. The dilute solution of iodophor that must kill lower life forms must be non-toxic to the higher animals being treated which are in prolonged and intimate contact with the solution through sensitive gill and mucous membranes as well as through ingestion.

SUMMARY OF THE INVENTION

It is accordingly an object of the invention to provide a stable, water soluble, concentrate composition that will release iodine for control of microorganisms when added to water in very low concentrations and that will be harmless to higher animals such as fish, turtles and the like using that water.

It has now been found, in accordance with the invention, that iodine containing compositions can be prepared that are stable at room temperature, that are effective for prophylactic and therapeutic purposes in aquaculture at concentrations that are harmless to the animals being cultured.

The present invention comprises a composition including an ethylene glycol alkyl ether as a solubilizing agent; a first iodophor prepared by reacting a quaternary ammonium type cationic detergent with iodomethane; a second iodophor prepared by heating elemental iodine with either a sulfonate of a generally unsaturated fatty acid or an alkyl phenoxy polyethoxy alcohol; water; and phosphoric acid to yield a ph below 2.

DETAILED DESCRIPTION OF THE PREFERRED EMBODIMENTS

The following examples, which are given for illustrative purposes only, do not serve to limit the scope of the invention in any way. The proportions are given by weight.

EXAMPLE 1

| iodophor A (STABILIZER) | |
|---|---|
| iodomethane | 2 |
| cetyl pyridinium bromide | 1 |
| mixed together at room temperature | |
| iodophor B (SUPPLY) | |
| elemental iodine | 1 |
| oleic acid sulfonate | 5 |
| mixed together at 60° C. | |
| mix together the following: | |
| iodophor A | 5 |
| iodophor B | 48 |
| ethylene glycol monobutyl ether | 16 |
| water | 127 |
| 85% orthophosphoric acid | 122 |

Commercial grades of oleic acid sulfonate may have a mixture of other fatty acids both saturated and unsaturated.

EXAMPLE 2

| iodophor A (STABILIZER) | |
|---|---|
| iodomethane | 2 |
| cetyl pyridinium bromide | 1 |
| mixed together at room temperature | |
| iodophor C (SUPPLY) | |
| elemental iodine | 1 |
| alkyl phenoxyl polyethoxy alcohol | 5 |
| mixed together at 60° C. | |
| mix together the following | |
| iodophor A | 5 |
| iodophor C | 48 |
| ethylene glycol monobutyl ether | 16 |
| water | 127 |
| 85% orthophosphoric acid | 122 | alkyl phenoxyl polyethoxy alcohol is exemplified by octoxynol, available commercially under various tradenames including Triton X-100 from Rohm and Haas.

Solutions as shown above have sufficient anti-foaming properties for most applications. For certain applications such as fountains, additional anti-foaming action may be economically conferred by the addition of small amounts of silicone anti-foaming agents.

The above disclosed invention has a number of particular features which should preferably be employed in combination although each is useful separately without departure from the scope of the invention. While I have shown and described the preferred embodiments of my invention, it will be understood that the invention may be embodied otherwise than as herein specifically illustrated or described, and that certain changes in the form and arrangement of parts and the specific manner of practicing the invention may be made within the underlying idea or principles of the invention within the scope of the appended claims.

I claim:

1. A stable biocidal iodophor liquid solution composition comprising:
   (a) a first iodophor formed from iodomethane and a soluble quaternary ammonium cationic surfactant mixed in a ratio of one part surfactant to about two parts of iodomethane;
   (b) a second iodophor formed by heating elemental iodine with a surfactant selected from the group consisting of a sulfonate of substantially olefinic fatty acid and alkyl phenoxyl polyether alcohol in a ratio of one part of iodine to between three and eight parts of surfactant;

(c) ethylene glycol alkyl ether;
(d) water;
(e) phosphoric acid sufficient to reduce the pH to below 1.6 and in which there is between 1 and 5 parts by weight of said first iodophor; between 20 and 70 parts by weight of said second iodophor; and between 10 and 25 parts by weight of said ethylene glycol alkyl ether;

wherein said composition, when greatly diluted releases iodine slowly to kill lower life forms including virus, fungi, bacteria and unicellular pathogens while remaining non-toxic to multicellular higher life forms including vetebrates.

2. The composition according to claim 1, in which said cationic surfactant is cetyl pyridinium bromide.

3. The composition according to claim 1, in which said alkyl phenoxyl polyether is octoxynol.

4. The composition according to claim 1, in which said ethylene glycol alkyl ether is ethylene glycol monobutyl ether.

5. The composition according to claim 1 including a silicone anti-foaming agent in amounts less than one half of one percent.

* * * * *